(12) United States Patent
Herrmann

(10) Patent No.: US 10,470,723 B2
(45) Date of Patent: Nov. 12, 2019

(54) X-RAY DEVICE WITH REDUCED PILE-UP

(71) Applicant: KONINKLIJKE PHILIPS N.V., Eindhoven (NL)

(72) Inventor: Christoph Herrmann, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 132 days.

(21) Appl. No.: 15/580,290

(22) PCT Filed: Jun. 23, 2016

(86) PCT No.: PCT/EP2016/064497
§ 371 (c)(1),
(2) Date: Dec. 7, 2017

(87) PCT Pub. No.: WO2017/001269
PCT Pub. Date: Jan. 5, 2017

(65) Prior Publication Data
US 2018/0160989 A1 Jun. 14, 2018

(30) Foreign Application Priority Data
Jun. 30, 2015 (EP) .................................... 15174564

(51) Int. Cl.
*A61B 6/00* (2006.01)
*A61B 6/03* (2006.01)
(Continued)

(52) U.S. Cl.
CPC ............ *A61B 6/032* (2013.01); *A61B 6/4241* (2013.01); *A61B 6/482* (2013.01); *A61B 6/54* (2013.01);
(Continued)

(58) Field of Classification Search
CPC ....... A61B 6/032; A61B 6/4241; A61B 6/482; A61B 6/54; A61B 6/06; A61B 6/4035;
(Continued)

(56) References Cited

U.S. PATENT DOCUMENTS 7,227,924 B2 6/2007 Zhou
2007/0290142 A1 12/2007 Du
(Continued)

FOREIGN PATENT DOCUMENTS

| EP | 2371288 | 10/2011 |
|---|---|---|
| JP | 2014048171 | 3/2014 |
| WO | 2012035466 | 3/2012 |

*Primary Examiner* — Kiho Kim
(74) *Attorney, Agent, or Firm* — Larry Liberchuk

(57) ABSTRACT

The invention relates to an x-ray device (1) for imaging an object (41). A radiation detector (3) of the x-ray device includes detector elements (21) for detecting radiation, each detector element (21) comprising an adjustable sensitive volume, where an x-ray photon entering the sensitive volume produces an electric signal used for generating the image data. Further, the device comprises a control unit (9) configured to control the sensitive volume of at least one of the detector elements (21) in accordance with a geometric structure of the object (41) to be imaged in order to reduce a pile-up effect in the detector element. Moreover, the invention relates to a method for operating the device (1) and to a computer program for carrying out the method.

15 Claims, 4 Drawing Sheets

(51) Int. Cl.
*G01T 1/24* (2006.01)
*G01T 1/17* (2006.01)
*H01L 27/146* (2006.01)
*A61B 6/06* (2006.01)

(52) U.S. Cl.
CPC ............... *G01T 1/17* (2013.01); *G01T 1/171* (2013.01); *G01T 1/24* (2013.01); *H01L 27/14676* (2013.01); *A61B 6/06* (2013.01); *A61B 6/4035* (2013.01); *A61B 6/4085* (2013.01); *A61B 6/488* (2013.01)

(58) Field of Classification Search
CPC ........... A61B 6/488; G01T 1/17; G01T 1/171; H01L 27/14676
See application file for complete search history.

(56) References Cited

U.S. PATENT DOCUMENTS

| | | |
|---|---|---|
| 2011/0017918 A1 | 1/2011 | Baeumer |
| 2011/0049376 A1 | 3/2011 | Zhang |
| 2014/0183371 A1 | 7/2014 | Roessl |
| 2015/0003589 A1 | 1/2015 | Kim |
| 2015/0063527 A1 | 3/2015 | Daerr |
| 2015/0253437 A1* | 9/2015 | Goderer ................. G01T 1/247 378/207 |

* cited by examiner

X-RAY DEVICE WITH REDUCED PILE-UP

CROSS REFERENCE TO RELATED APPLICATIONS

This application is the U.S. National Phase application under 35 U.S.C. § 371 of International Application No. PCT/EP2016/064497 filed Jun. 23, 2016, published as WO 2017/001269 on Jan. 5, 2017, which claims the benefit of European Patent Application Number 15174564.3 filed Jun. 30, 2015. These applications are hereby incorporated by reference herein.

FIELD OF THE INVENTION

The invention relates to an x-ray device for imaging an object. More specifically, the invention relates to an x-ray device for acquiring image data of an object to be imaged, the device comprising an x-ray source and a radiation detector. Further, the invention relates to a method for operating an x-ray device to acquire image data of an object to be imaged and to a computer program for carrying out the method. In particular, the x-ray device may be a photon-counting computed tomography (CT) device.

BACKGROUND OF THE INVENTION

So-called photon-counting or spectral x-ray devices allow for detecting single x-ray photons hitting the radiation detector separately and for determining the energies of the incident photons in accordance with plural energy bands or "bins". However, when two or more photons arrive at the radiation detector within a time interval that is shorter than the so-called deadtime of the detector, they are registered as a single event with a very high (wrong) energy. This effect, which is also known as pile-up effect, results in lost counts and in a distorted energy spectrum.

Also in view of the pile-up effect, the intensity of the x-ray beam may be selected such that the photon flux rate in the beam arriving at the detector after having been attenuated by the object to be imaged is not too high so that pile-up is avoided. However, also after a corresponding adaptation of the beam intensity pile-up does usually still occur in regions of the radiation detector collecting parts of the x-ray beam which are not or only weakly attenuated. This is particularly the case for parts of the beam which travel next to (and not through) the object to be imaged or which traverse only weakly attenuating regions of the object, such as, for example, lung tissue in case the object to be imaged is a human or animal body.

In order to reduce the pile-up effect for parts of the radiation detector receiving radiation directly from the x-ray source, beam-shaping filters—so-called bowtie filters—have been used for reducing the intensity of the parts of the radiation beam which do not traverse the object. However, in CT the relevant contour of the object varies, when the x-ray source and the radiation detector rotate around the object. Therefore, dynamic beam-shaping filters have to be used which allow for varying the beam shape during the rotation of the x-ray source and the radiation detector. Such dynamic filters are mechanically very complex and, thus, very expensive. Moreover, it is nearly impossible to attenuate the center of the x-ray beam using a beam-shaping filter as it would be necessary for imaging human legs, for example, or weakly attenuating regions within an object.

US 2011/0017918 A1 relates to a radiation detector that is suited for energy resolved single x-ray photon detection in a CT scanner. The detector comprises an array of scintillator elements in which incident x-ray photons are converted into bursts of optical photons. Pixels associated with the scintillator elements determine the number of optical photons they receive within predetermined acquisition intervals. Detector cells of the radiation detector can be designed such that they change from a sensitive state to an insensitive state upon detection of a single optical photon, and the detector cells are reset to the sensitive state during a reset interval. The duty cycle including the acquisition time and the reset time can be adapted to the detected flux. Thus, the pile-up effect may be reduced. However, upon having changed to the insensitive state, a detector cell can no longer detect photons until it is reset.

EP 2 371 288 A1 relates an imaging system comprising a radiation source and a detector. The system determines parameters associated with the radiation source and the detector based on a priori information and preliminary image data. With respect to the detector, the system may switch detector elements between a photon-counting and an energy-integrating mode based on the flux determined using the preliminary image data. US 2015/0063527 is related to an x-ray system comprising a photon-counting detector array of detector pixels that include direct conversion material. In order to determine the correct input photon count rate, multiple input photon count rates are mapped to a single output photon count rate. Then, the image data are reconstructed on the basis of the determined input photon count rate.

SUMMARY OF THE INVENTION

It is an object of the present invention to allow for a less complex reduction of the pile-up effect in an x-ray radiation detector. Further, it is an object of the invention to reduce time intervals in which the x-ray radiation detector cannot detect radiation.

In a first aspect of the present invention, an x-ray device for acquiring image data of an object to be imaged is suggested. The device comprises an x-ray source and a radiation detector. The radiation detector includes detector elements for detecting radiation, each detector element comprising an adjustable sensitive volume, where an x-ray photon entering the sensitive volume produces an electric signal used for generating the image data. The device further comprises a control unit configured to control the sensitive volume of at least one of the detector elements in accordance with a geometric structure of the object to be imaged.

Since the sensitive volume of one or more detector element(s) can be controlled in accordance with the geometric structure of the object to imaged, it is possible to adapt the sensitive volume of the detector element(s) to the incident photon flux in such a way that the pile-up effect can be reduced or avoided. A complex dynamic bowtie filter for adapting the photon flux can be dispensed with. Further, it is also possible to adapt the sensitive volume of the detector element(s) in accordance with more complex geometric structures of the object to be imaged to which a mechanical filter cannot be adequately adapted.

Here, the term detector element particularly relates to a part of the radiation detector which comprises a sensitive volume that can be adjusted separately from the sensitive volumes of other parts of the radiation detector (i.e. other detector elements).

By controlling the sensitive volume of one or more detector element(s) in accordance with the geometric structure of the object to be imaged, it is particularly possible to reduce the sensitive volume of the detector element(s) when these detector element(s) is/are exposed to a direct photon flux from the x-ray source or to an only weakly attenuated x-ray photon flux. Hereby, the pile-up effect in these detector elements can be avoided or at least significantly reduced. At the same time, detector elements exposed to a lower photon flux may be operated with a larger, "normal" sensitive volume to thereby optimize the energy resolution of these detector elements.

The geometric structure to which the sensitive volume of the detector element(s) can be adapted may particularly comprise the three-dimensional (outer) contour of the object to be imaged. In this respect, one embodiment of the invention provides that the control unit is configured to reduce the sensitive volume of the detector element when at least part of the detector element is located outside a shadow region created by the object in accordance with a geometric structure of the object. The shadow region created by the object corresponds to the region, which can only be reached by x-ray radiation emitted by the x-ray source after having traversed the object. Thus, it is possible to reduce the pile-up effect for detector elements which collect radiation directly travelling from the x-ray source to the radiation detector without traversing the object.

In addition or as an alternative, the geometric structure to which the sensitive volume of the detector element(s) is adapted may comprise the contour of regions within the object to be imaged, which have a low x-ray attenuation coefficient. In case the object is a human or animal body, one example for such a region is the lung. In view of such regions, a further embodiment of the invention includes that the control unit is configured to reduce the sensitive volume of the detector element when at least part of the detector element collects radiation having traversed a region of the object having a smaller x-ray attenuation coefficient than another region of the object.

Optionally, the x-ray device may be configured as a CT device. In this case, the x-ray source and the radiation detector are configured to rotate around the object during an x-ray scan of the object.

In one related embodiment of the invention, a control profile indicates values of a control parameter for controlling the sensitive volume of the detector element for several positions of the radiation detector during the x-ray scan and the control unit controls the sensitive volume of the detector element by varying the control parameter in accordance with the values of the parameter indicated in the control profile. The control profile may be generated before the actual x-ray scan is executed. Therefore, a related embodiment provides that the control unit is coupled to a storage for storing the control profile and that the control unit reads the control profile in connection with an execution of the x-ray scan.

In one embodiment, the control unit is configured to generate the control profile on the basis of one or more images of the object acquired in a further x-ray scan. The further x-ray scan may particularly be a scout scan executed with reduced radiation intensity. Often, such a scout scan is already executed for planning "conventional" CT scans so that no additional scans have to be performed in order to determine the control profile for controlling the sensitive volume of the detector elements. Moreover, the images generated during a scout scan show the shadow regions produced by the object and can also show internal geometric structures of the objects (particularly of weakly attenuating regions of the object) so that such geometric structures can be taken into consideration when generating the control profile.

In embodiments of the invention, the control profile is generated in accordance with an estimated geometric structure of the object. In particular, the geometric structure of the object may be estimated by the control unit on the basis of measurement data indicative of the geometric structure of the object. In a related embodiment of the invention, the CT device further comprises a rangefinder configured to scan the object, and the control unit is configured to estimate the geometric structure of the object on the basis of dimensions of the object determined using the rangefinder. By means of such a rangefinder, i.e. a device for measuring distances, it is possible to determine the outer contour of the object to be imaged without exposing the object to x-ray radiation.

Further, one embodiment of the invention provides that the estimated geometric structure of the object corresponds to a fixed predetermined geometric structure. In a related embodiment, predetermined control profiles for geometric structures for plural classes of the object are stored in the control unit and the control unit is configured to select the control profile on the basis of a piece of information about the class of the object to be imaged. In these embodiments the control profile for controlling the sensitive volume of the detector element can usually not be adapted to the actual geometric structure of the object as accurately as in the aforementioned embodiments. However, it is not necessary to have the control profile be generated by the control unit on the basis of measured data. Rather, predetermined fixed control profiles generated in accordance with predetermined geometric structures may be produced and pre-stored in the control unit. For each object to be imaged, the control unit may then select the control profile pertaining to the geometric structure for the class of the object.

In one embodiment, the detector element comprises a converter element producing electric charge carriers in response to an incident photon, the converter element being arranged between a cathode electrode assembly and an anode electrode assembly. The anode electrode assembly may comprise at least one anode electrode for collecting charge carriers to produce an electric signal used for generating the image data and at least one steering electrode which can be held on the same or a more negative electric potential than the anode electrode. In such a detector element, the sensitive volume can be adjusted by varying the voltage (i.e. potential difference) between the anode electrode(s) and the steering electrode(s), because a variation of this voltage changes the electric field between the cathode electrode assembly and the anode electrode assembly within the converter element. In particular, the sensitive volume of the detector element can be reduced by bringing the electric potential of the steering electrode closer to the electric potential of the anode electrode or by making it more positive than the anode electrode potential.

In a related embodiment, a control profile indicates values of a parameter indicative of a voltage between the anode electrode and the steering electrode for several positions of the radiation detector during an x-ray scan, and the control unit is configured to control the sensitive volume of the detector element by varying the voltage in accordance with the values of the parameter indicated in the control profile.

In a further aspect of the invention, a method for operating an x-ray device to acquire image data of an object to be imaged is proposed, the device comprising an x-ray source and a radiation detector, the radiation detector including detector elements for detecting radiation, each detector element comprising an adjustable sensitive volume, where an x-ray photon entering the sensitive volume produces an electric signal used for generating the image data. In the method, a control unit of the device controls the sensitive volume of at least one of the detector elements in accordance with a geometric structure of the object to be imaged.

In a further aspect of the invention, a computer program is presented, which is executable in a processing unit of an x-ray device according to the invention and its embodiments. The computer program comprises program code means for causing the processing unit to carry out a method according to the invention or its embodiments when the computer program is executed in the processing unit.

It shall be understood that the x-ray device of claim 1, the method of claim 14 and the computer program of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
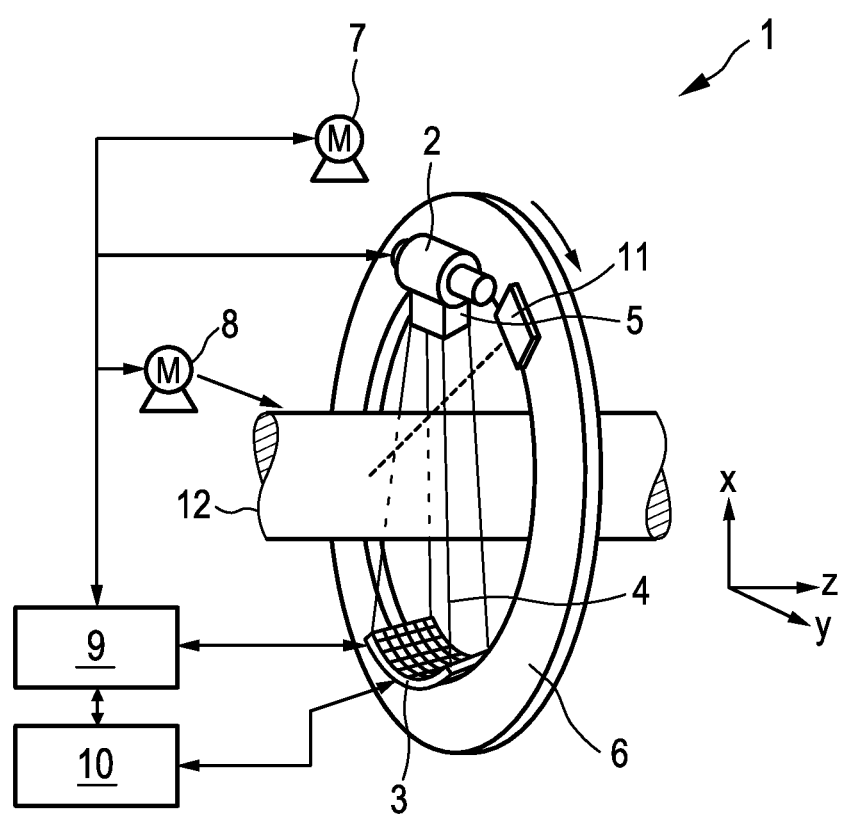
FIG. 1 shows schematically and exemplarily an x-ray apparatus according to the invention, which is particularly configured as a CT apparatus.

FIG. 1 schematically and exemplarily illustrates components of a CT apparatus 1 for imaging an object. In one embodiment, which will also be referred to herein below, the object is a patient body or a part of the patient body. However, the CT apparatus 1 may likewise be used to image other objects.

The CT apparatus 1 comprises an x-ray source 2, such as an x-ray tube, and a radiation detector 3. The x-ray source 2 produces an x-ray beam 4 which traverses an examination region 12 between the x-ray source 2 and the radiation detector 3 before x-ray radiation is collected by the radiation detector 3. The x-ray beam 4 may be a cone beam or may have another beam shape, such as a fan shape. For shaping the x-ray beam, the x-ray source 2 may be provided with a suitable collimator 5. The radiation detector 3 is configured as a photon-counting detector which is capable of detecting single incident x-ray photons and allows for determining their energies in accordance with a number of predefined energy bins. In this regard, a photon incident into the radiation detector 3 generates electric charges in accordance with its energy and induces a pulse signal with a height depending on the photon energy, which can be collected.

The x-ray source 2 and the radiation detector 3 are mounted at opposing positions on a rotatable gantry 6 which is driven by a motor 7. By means of the motor 7, the gantry 5 can be rotated such that the x-ray source 2 and the radiation detector 3 can be rotated around an object to be imaged positioned within the examination region 12. The object is placed on a support (not shown in the figure) which can be positioned in the examination region 12. In case the object is a patient body, the support may be configured as a patient table. By moving the object and the gantry 6 relative to each other in the direction of the z-axis, i.e. perpendicular to the beam direction, different so-called slices of the object can be imaged. For this purpose, the support (and, thus, the object) may be displaced back and forth within the examination region 12 in the direction of the z-axis by means of a further motor 8. However, it is also possible that the support is not moved, but that the gantry 6 can be displaced in the direction of the z-axis.

The x-ray source 2 and the radiation detector 3 are coupled to a control unit 9 controlling the operation of the x-ray source 2 and the radiation detector 3. With respect to the x-ray source 2, the control unit 9 particularly controls timing and power for generating x-ray radiation. With respect to the radiation detector 3, the control unit 9 particularly controls the sensitive volume of detector elements 21 of the radiation detector 3 in a way to be explained in more detail further below. Moreover, the control unit 9 controls the motors 7 and 8 driving the gantry 6 and the object support. The radiation detector 3 is further coupled to a reconstruction unit 10 which reconstructs images on the basis of the measurement data collected by the radiation detector 3. These measurement data are usually projections of the object, and images can be reconstructed from these projections in a way known to a person skilled in the art. Since an energy-discriminating photon-counting detector 3 is used, it is possible to create separate images for each energy range or bin.

The control unit 9 and the reconstruction unit 10 may be configured as computer devices which comprise processor units to execute computer programs implementing the routines carried out by the control unit 9 and the reconstruction unit 10. In one embodiment, the control unit 9 and the reconstruction 10 are implemented in separate computer devices. However, it is likewise possible that the control unit 9 and the reconstruction unit 10 are included in a single computer device and implemented in several processor units or a single processor unit of the computer device.

Figure 2:
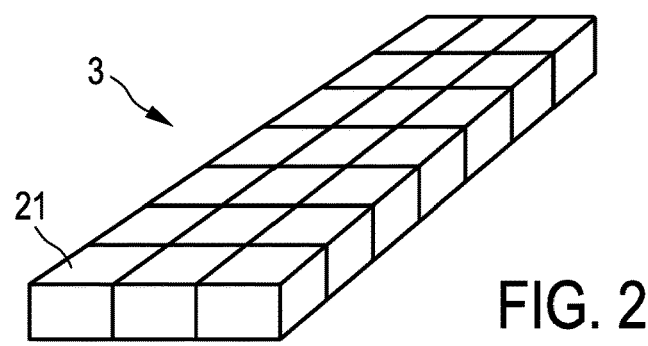
FIG. 2 shows schematically and exemplarily plural detector elements of the radiation detector of the x-ray apparatus.

As schematically and exemplarily illustrated in FIG. 2, the radiation detector 3 comprises a plurality of detector elements 21, which are sometimes also referred to as modules or tiles and which are preferably arranged in an array which may be flat or concave. Thus, the detector elements 21 are arranged in the form of rows and columns arranged perpendicular to each other.

Each detector element 21 comprises a converter element 31 for converting X-rays into electrical signals, which element is provided between a cathode contact assembly 32 and an anode contact assembly 33. The converter element 31 is made of a semiconductor material, where suitable semiconductor materials are, for example, silicon (Si), cadmium telluride (CdTe), cadmium zinc telluride (CZT), mercury iodide (HgI) and gallium arsenide (GaAs). The cathode contact assembly 32 is generally held on a lower electric potential than the anode contact assembly 33 (i.e. a negative voltage is applied to the cathode contact assembly 32 with respect to the anode contact assembly 33) so that an electric field is formed between the cathode contact assembly 32 and the anode contact assembly 33 within the converter element 31. The cathode side of the detector element 31 may point towards the x-ray source 2 so that x-ray photons enter into the converter element 31 through the cathode assembly 32 and so that the electric field is parallel to the (main) beam direction. However, it is likewise possible that the detector element is configured in another way.

In one embodiment, the converter element 31 may be configured as a cubic block and its lateral dimensions may be much larger than its thickness. For instance, the length and width of the converter element 31 may be between 10 and 20 mm, and the converter element 31 may have a thickness of about 2-3 mm. The cathode contact assembly 32 and the anode contact assembly 33 may be connected to the large top and bottom sides of the converter element 31 so that the electric field extends along the smaller thickness direction of the converter element 31. Further, the cathode contact assembly 32 may be configured as a continuous cathode electrode, which may be formed by a thin metalized film applied onto the converter element 31. In contrast, the anode assembly 33 may include pixelated anode electrodes 34, i.e. separated anode electrodes 34 which are arranged in certain distances to each other and which are usually also referred to as anode pixels. Such anode pixels may have a diameter between 50 μm and 1 mm, for example.

The anode electrodes or pixels 34 are used for collecting electric pulses produced by photons incident on the converter element 31 and are connected to readout electronics (not shown in the figures) which collect the electric pulses and determine the measurement data which are subsequently provided to the reconstruction unit 10. Thus, when an x-ray photon enters into the converter element 31, it excites the semiconductor material and thereby generates electric charge carriers (electrons and holes). The negative charge carriers drift to one of the anode electrodes 34 under the influence of the electric field in the converter element 31 and produce the aforementioned electric pulse collected by the read-out electronics.

In this conversion process, each anode electrode 34 collects the charge carriers produced in an associated region of the converter element 31 in the vicinity of the anode electrode 34, while charge carriers produced in other regions of the converter element 31 are collected by other anode electrodes 34. The region from which one anode electrode 34 collects generated charge carriers is also referred to as sensitive volume of the anode electrode 34 herein. Together, the sensitive volumes pertaining to the anode electrodes 34 of one detector element 21 form the sensitive volume of the detector element 21. In this respect, it is also to be understood that the sensitive volume pertaining to one of the anode electrodes 34 of a detector element 21 may overlap with the sensitive volume pertaining to another anode electrode 34 of the same detector element 21, when the anode electrodes 34 are configured as pixilated electrodes as explained above.

Figure 3A:
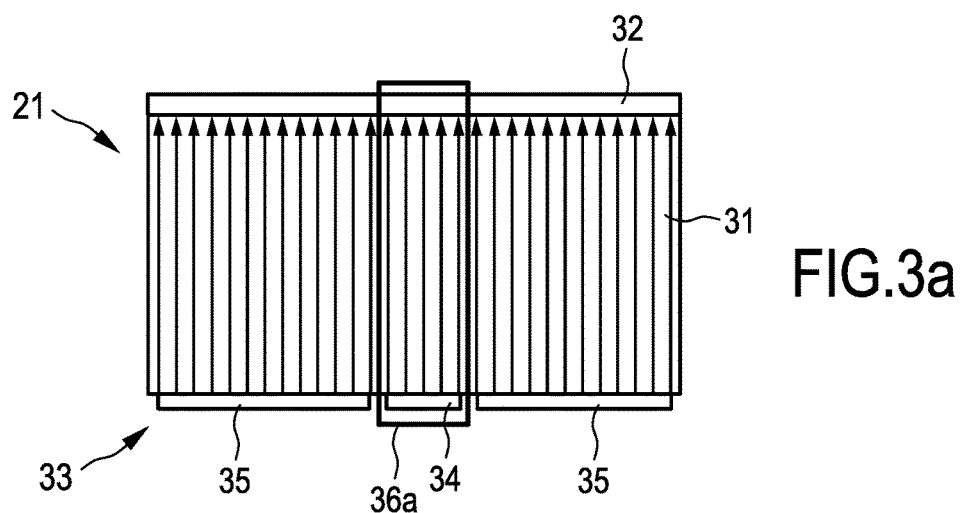
FIG. 3a shows schematically and exemplarily an electric field in a section of one detector element, when steering electrodes are floating.
Figure 3B:
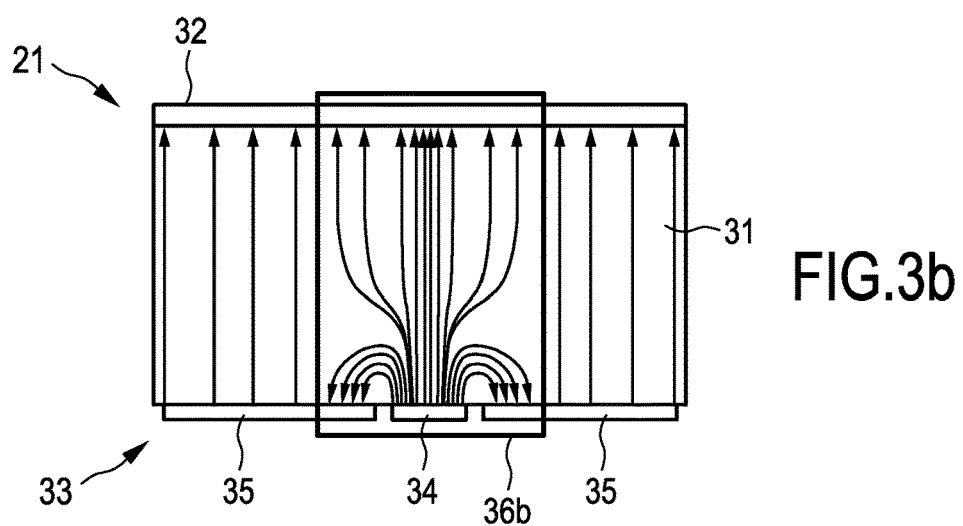
FIG. 3b shows schematically and exemplarily an electric field in the same section of the detector element, when the steering electrodes have a lower electric potential than the anode electrode.

In the radiation detector 3, the sensitive volumes of anode electrodes 34 and, thus, the sensitive volumes of the detector elements 21, can be adjusted. For this purpose, steering electrodes 35 may be provided. These steering electrodes 35 are not connected to the readout electronics so that electric charges collected by the steering electrodes 35 are not taken into consideration by the reconstruction unit 10 when reconstructing images. In one embodiment, the steering electrodes 35 may be arranged at the converter elements 31 of the detector elements 21 on the same side as the anode electrodes 34 and adjacent to the anode electrodes 34. In particular, the steering electrodes 35 may be configured as circular shaped electrodes, where each steering electrode 35 encircles one associated anode electrode 34. Such an embodiment is schematically and exemplarily illustrated in FIGS. 3a and 3b, showing a section of a detector element 21 comprising one anode electrode 34 and one steering electrodes 35 surrounding the anode electrode 34. In this embodiment, the sensitive volume of the anode electrodes 34 of a detector element 21 can be controlled by varying the voltage between the anode electrodes 34 and the steering electrodes 35. The sensitive volume of the anode electrodes 34 can be increased by lowering the electric potential of the steering electrodes 35 relative to that of the anode electrodes 34. Since with floating steering electrodes 35, a certain open circuit voltage (usually more negative than the anode potential) between the steering electrodes 35 and the anode electrodes 34 results, an increase of the sensitive volume relative to the case of a floating steering electrodes 35 can only be achieved by choosing a steering electrode potential that is more negative than the open circuit voltage. The mechanism governing the adjustment of the sensitive volume of a detector element 21 is further illustrated in FIGS. 3a and 3b.

In the situation shown in FIG. 3a, the steering electrode 35 is held on the same electric potential as the anode electrode 34. Here, the field lines of the electric field within the converter element 31 extend in parallel from the electrode assembly 33 to the cathode electrode 32. As a consequence, the anode electrode 34 does only collect charge carriers generated within a volume which is approximately determined by the volume the projection of which to the anode side results in the anode area 32. In FIG. 3a, the box 36a illustrates this sensitive volume. In the situation illustrated in FIG. 3b, the steering electrode 35 has a lower electric potential than the anode electrode 34. As a consequence, the electric field lines are deformed such that the electric field lines starting on the anode electrode 34 extend through a larger volume compared with the aforementioned situation in which the steering electrode 35 is held on the same potential as the anode electrode 34. Thus, the sensitive volume pertaining to the anode electrode 34 is increased. In FIG. 3b, the box 36b illustrates this increased sensitive volume.

The steering electrodes 35 of the detector elements 21 of the radiation detector 3 are coupled to the control unit 9 in order to allow the control unit 9 to vary the electric potentials of the steering electrodes 35 relative to the electric potentials of the anode electrodes 34 and, thus, to vary the sensitive volume of the detector elements 21. Preferably, the control unit 21 can control the sensitive volume of each detector element 21 separately from the sensitive volumes of the other detector elements 21 of the radiation detector 3. Thus, the control unit 21 is capable of controlling the electric potential of the steering electrodes 35 of a detector element 21 together and separately from the electric potentials of the steering electrodes 35 of the other detector elements 21. Further, one embodiment provides that the control unit 9 is capable of controlling the steering electrode potential in accordance with several predefined values. For instance, it may be possible for the control unit 9 to select one of the values 0V, −50V and −70V for the voltage between the anode electrodes 34 and the steering electrodes 35 of a detector element 21.

In order to reduce the pile-up effect in the radiation detector 3, the control unit 9 controls the sensitive volumes of the detector elements 21 of the radiation detector 3 such that the detector elements 21 which are exposed to a high photon flux have a reduced sensitive volume compared with the detector elements 21 which are exposed to a lower photon flux. In this respect, the controlling of the sensitive volume of the detector elements 21 is based on the geometrical structure of the object to be imaged. So, a detector element 21 is exposed to a high photon flux when it is outside the shadow region of the object on the detector surface of the radiation detector 3. Further, an object to be imaged may include regions having a lower attenuation coefficient for x-rays than other regions of the object. Thus, when collecting x-ray radiation having traversed a region with a lower attenuation coefficient, a detector element 21 is exposed to a higher photon flux.

In view of these findings, the control unit 9 particularly reduces the sensitive volume of each detector element 21 of the radiation detector 3, when the detector element 21 is outside the shadow region of the object created on the detector surface of the radiation detector 21. Thus, the sensitive volume of a detector element 21 collects radiation which directly travels from the x-ray source 2 to the radiation detector 3 without traversing the object to be imaged. If a part of a detector element 21 is outside the shadow region and another part of the detector element 21 is within the shadow region, the sensitive volume is preferably also reduced; otherwise, the partly exposure to the high direct photon flux may result in a pile-up effect within the detector element 21. Thus, the control unit 9 does preferably reduce the sensitive volume of each detector element 21 which is at least partly exposed to direct photon flux from the x-ray source 2.

Figure 4:
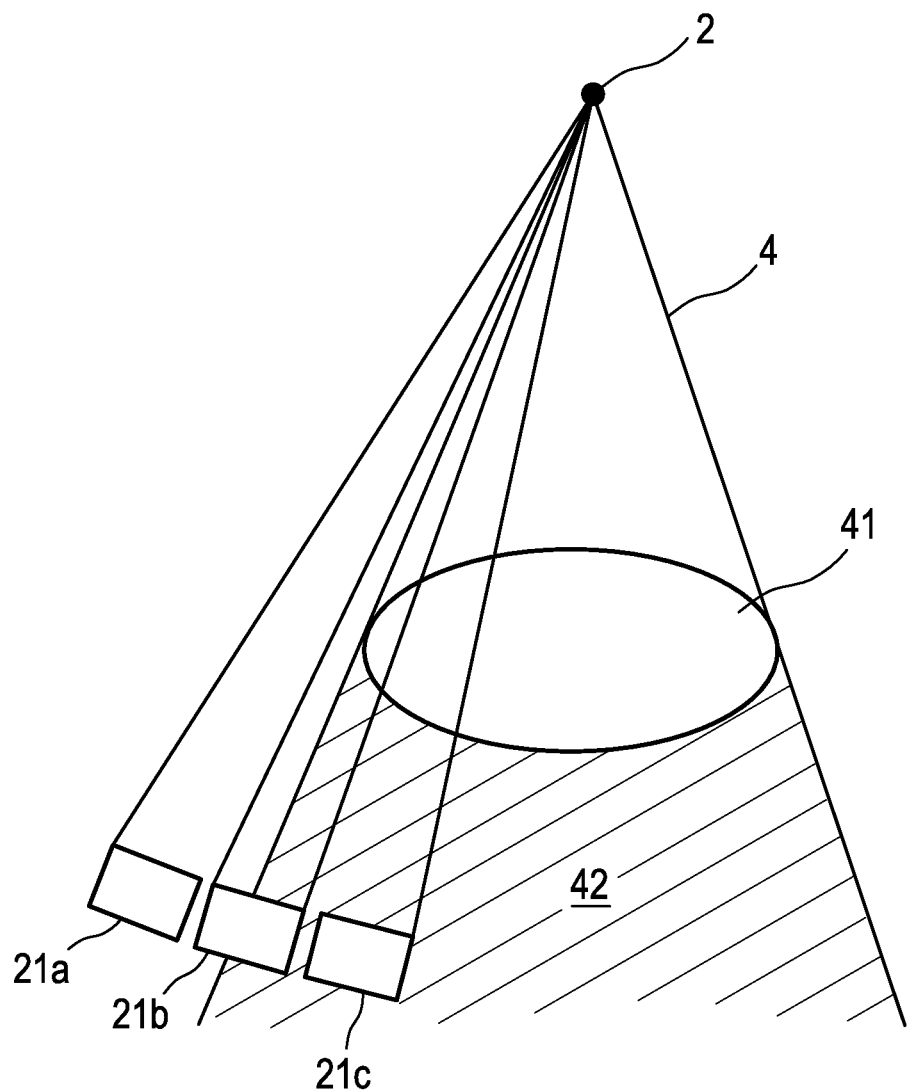
FIG. 4 shows schematically and exemplarily detector elements of the radiation detector which are inside and outside a shadow region of an object to be imaged in one particular position of the radiation detector.

This is schematically and exemplary illustrated in FIG. 4. For one particular slice, i.e. for one z-position, FIG. 4 illustrates the corresponding cross section of an object 41. Further, FIG. 4 shows the x-ray source 2 emitting an x-ray beam 4 which partly traverses the object 41 and which does partly not traverse the object 41 so that the object 41 creates a shadow region 42 shown as hatched area in FIG. 4. By way of example, FIG. 4 further shows three detector elements 21*a*, 21*b* and 21*c* in accordance with a particular position of the x-ray source 2 and the radiation detector 3. At this position, the detector element 21*c* is within the shadow region 42 and, thus, collects radiation that has traversed the object 41. Therefore, the control unit 9 configures the detector element 21*c* to have a "normal", i.e. unreduced, sensitive volume. The detector element 21*a* is outside the shadow region 42 and, thus, is exposed to direct photon flux from the x-ray source 2. The detector element 21*b* is partly outside the shadow region 42. Consequently, the control unit 9 configures the detector element 21*a* and preferably also the detector element 21*b* to have a reduced sensitive volume compared to the detector element 21*c*.

Since the x-ray source 2 and the radiation detector 3 rotate around the object 412 in CT, the radiation exposure of the individual detector elements 21 may change during a CT scan. Therefore, the sensitive volume of the detector elements 31 may have to be varied during a CT scan. This variation is preferably controlled by the control unit 9 using control profiles, which may be stored in the control unit 9 before executing the CT scan. Each of these control profiles may be assigned to one of the detector elements 21 and may specify the steering electrode voltages for the assigned detector element 21 for the different positions of the x-ray source 2 or the gantry 6 during the CT scan. In particular, the control profile may specify the steering electrode voltage as a function of the angular position of the gantry 6 or a comparable parameter for each slice examined during the CT scan. In one embodiment, one control profile with such content may be stored in the control unit 9 for each detector element 21 of the radiation detector 3. In a further embodiment, the control unit 9 may store one control profile for each detector element 21 which leaves the shadow region 42 of the object 41 during the CT scan (if a detector element 21 remains in the shadow region during the CT scan, as it may be the case for central detector elements 21, no control profile is stored for this detector element 21 in this embodiment).

Figure 5:
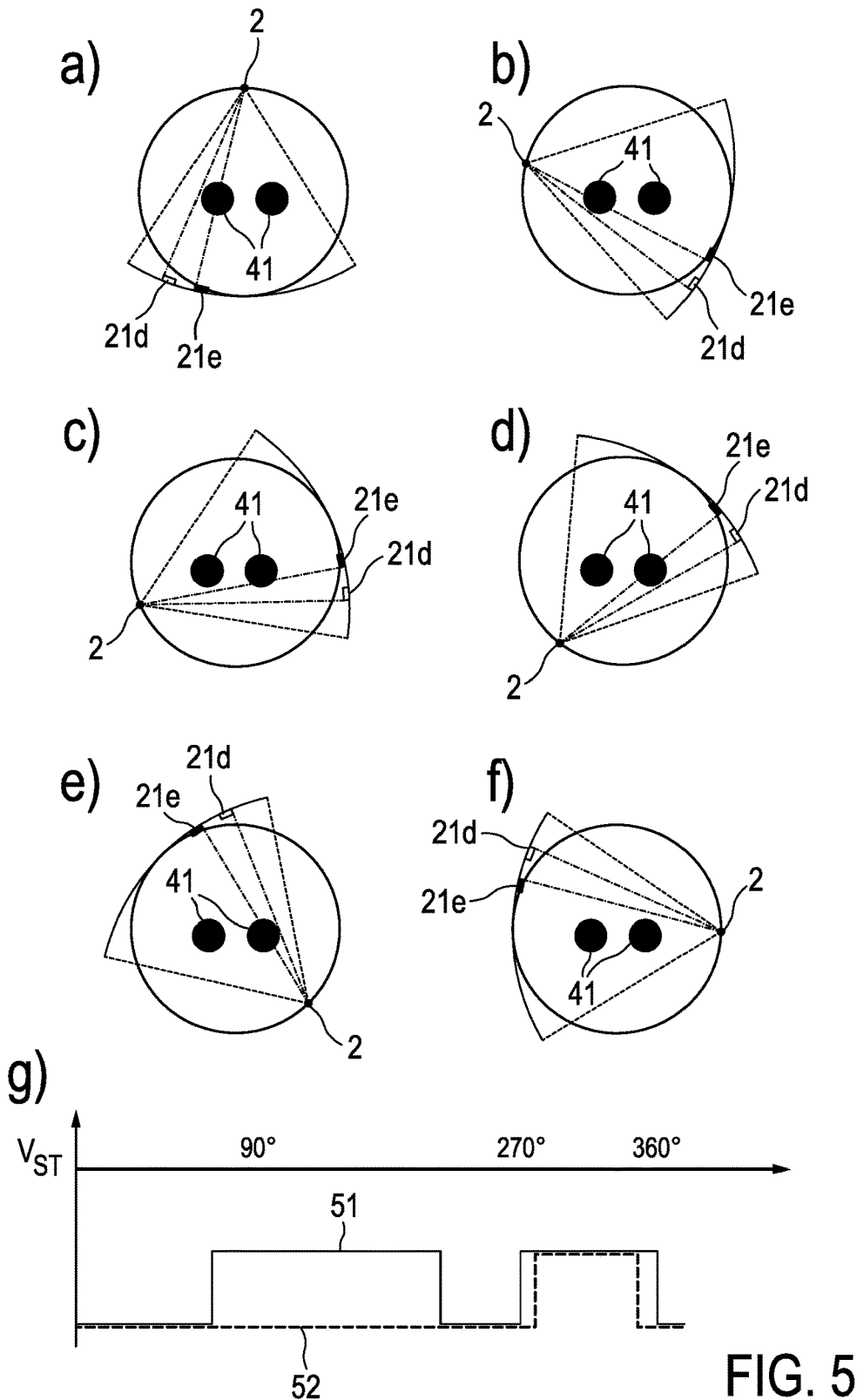
FIGS. 5a-f show schematically and exemplarily the relative positions of two detector elements with respect to legs as an object to be imaged for one slice and different angular positions of the radiation detector.
FIG. 5g shows schematically and exemplarily a diagram illustrating a voltage between the steering electrode and an anode electrode of the detector elements shown in FIGS. 5a-f as a function of the angular position of the radiation detector.

FIG. 5 schematically illustrates exemplary control profiles for two detector elements 21*d* and 21*e* for imaging an object 41 comprising human legs using the CT apparatus 1: In FIGS. 5*a*-5*f*, the two detector elements 21*d* and 21*e* are depicted for one slice and various angular positions of the gantry 6. FIG. 5*g* includes a diagram showing the steering electrode voltage $V_{ST}$ as a function of the angular positions in this slice as specified in the control profiles pertaining to the detector elements 21*d* and 21*e*, where the curve 51 represents the control profile for the detector element 21*d* and the curve 52 represents the control profile for the detector element 21*e*. As can be seen in FIG. 5*g*, the steering electrode voltage $V_{ST}$ is increased and, thus, the sensitive volume of the detector element 21*d*; 21*e* is reduced, when the detector element 21*d*; 21*e* is outside the shadow region 42 of the legs.

In one embodiment, the control profiles for controlling the sensitive volume of the detector elements 21 are determined on the basis of the contour of the object 41 to be examined. The object contour may be estimated before the actual CT scan is executed using the control profiles. For estimating the object contour, a CT scan with reduced radiation intensity may be made, i.e. a radiation intensity which is lower than the radiation intensity used in the actual CT scan. Such a CT scan is also referred to as scout CT scan herein. During the scout CT scan, the object 41 is exposed to a significantly lower radiation dose than during a "full" CT scan. Further, scout CT scans are often already included in CT examination routines in order to plan the actual CT scan, e.g. to select the slices to be imaged in the actual CT scan. Thus, it is often not necessary to perform an additional scan for determining the control profiles.

In order to determine the control profiles, the x-ray source 2 and the radiation detector 3 may run through the same positions as in the actual CT scan. In a further embodiment, the x-ray source 2 and the radiation detector 3 may run through fewer positions compared with the actual CT scan. For such positions, the control profiles can be directly determined from the detector measurements at these positions, and with respect to the remaining positions of the actual CT scan, the control profiles may be determined using a suitable interpolation procedure.

At each relevant position, it may be determined for each detector element 21 whether the detector element 21 collects the full radiation intensity (i.e. is outside the shadow region 42 of the object 41) or collects no or a significantly reduced radiation intensity (i.e. is inside the shadow region 42 of the object 41). If it is determined for a position of the x-ray source 2 and the radiation detector 3 that a detector element 21 is at least partly outside the shadow region 42, a reduction of the sensitive volume is specified in the control profile of this detector element 21 for the position. Otherwise, i.e. when the detector element 21 does only register few or no radiation and, thus, is within the shadow region 42 at the position, the "normal" sensitive volume is specified in the control profile of the detector element 21 for this position.

Although the control profiles can be very accurately determined in the aforementioned way, the object 41 is exposed to a higher radiation dose in this embodiment. Therefore, further embodiments avoid the executing of a CT scan for determining the control profiles for controlling the sensitive volumes of the detector elements 21.

In one related embodiment, the three-dimensional contour of the object 41 to be imaged is determined using a three-dimensional laser scanner (shown in FIG. 1) or another optical or acoustical object scanner, which may optionally be mounted at the gantry 6. Such an object scanner, which may be configured in a way known to a person skilled in the art as such, also allows for an accurate determination of the actual three-dimensional contour of the object 41 to be imaged. In particular, the object scanner may comprise a rangefinder 11, such as, for example, a laser rangefinder, and for each relevant slice, the rangefinder 11 may be used to measure the distance along the beam direction to the next object for several angular positions. On the basis of these measurements, the control unit 9 may estimate the three-dimensional contour of the object. Then, the control unit 9 may determine for each position of the x-ray source 2 and the radiation detector 3 during the subsequent CT scan and for each detector element 21, whether the detector element 21 is inside or outside the shadow region of the object 42. This determination is made on the basis of the estimated three-dimensional object contour, the known positions of the detector elements 21 relative to the object contour and the x-ray source and the known shape of the radiation beam 4. As a result of this determination, the control unit 9 generates the control profiles for controlling the sensitive volume of the detector elements 21 such that the sensitive volume of a detector element 21 will be reduced at positions at which the detector element 21 is at least partly outside the shadow region 42 of the object 41.

In a further embodiment, a determination of the actual dimensions of the object 41 is dispensed with. Rather, the control unit 9 may store predefined control profiles for different object classes. The object classes include typical types of objects which are imaged using the CT apparatus 1. If the CT apparatus 1 is used in medical applications, the object types may include the thorax of a human or animal body, the complete upper part of the body and the extremities, such as human legs, for example. Optionally, such types of objects may also be subdivided into subtypes according to predefined criteria, such as their dimension, and each subtype may correspond to one object class to which control profiles are associated. Thus, different control profiles may be provided for the thorax of adults and children, for example.

For each object class, the associated control profiles may be generated on the basis of typical three-dimensional contours of objects of the relevant class. Preferably, the control profiles are particularly generated on the basis of three-dimensional contours which are smaller than the actual three-dimensional contours of the objects of the respective class. Hereby, a reduction of the pile-up effect can also be achieved in case a small object of a particular class is imaged using the CT apparatus 1. In this embodiment, the predefined control profiles stored in the control unit 9 can be used for controlling the sensitive volumes of the detector elements 21 without having to estimate the object contour in the control unit 9. Rather, the control unit 9 may directly select and load the control profiles stored for the class of the object 41 to be imaged. For this purpose, the object class may be input by the operator of the CT apparatus 1, for example.

In the aforementioned embodiments, the sensitive volume is reduced for detector elements 21 of the radiation detector 3, which are outside the shadow region 42 of the object 41 to be imaged, in order to reduce the pile-up effect for such detector elements 21. However, a pile-up effect can also occur with respect to detector elements 21 within the shadow region 42. In particular, a pile-up effect can occur in detector elements 21 collecting radiation which has traversed regions of the objects 41 having relative small x-ray attenuation coefficients. In case of human or animal bodies, one example of such a region is the lung.

Before this background, one embodiment provides that the sensitive volume of a detector element 21 is also reduced, when the detector element 21 collects radiation that has traversed a region of the object 41 which only weakly attenuates the x-ray radiation. The geometric structure of such a region may again be determined on the basis of the images acquired during the aforementioned scout CT scan which precedes the actual CT scan. Preferably, the radiation intensity during this scout CT scan is selected such that the radiation is not completely attenuated by body regions which have a low x-ray attenuation coefficient. When the radiation intensity is selected in such a way, it is particularly possible to identify detector elements 21 collecting radiation traversing such body regions at certain positions of the radiation detector 3. In the images generated during the scout CT scan, the control unit 9 may identify the relevant regions on the basis of increased photon count rates compared with other image regions. In particular, the control unit 9 may identify an image region corresponding to a region of the object with weak x-ray attenuation, when the photon count rate exceeds a predetermined threshold selected based on the emitted radiation intensity during the preceding CT scan.

In case the object contour is not determined by means of a scout CT scan, but on the basis of a scan of the object 41 by means of an object scanner, the control unit 9 may store three-dimensional shapes of typical types of object regions with a weak x-ray attenuation, such as, for example, the lung, and may estimate the dimensions of the actual region on the basis of dimensions of the object contour. On this basis, the control unit 9 may calculate the control profiles for controlling the sensitive volume of the detector elements 21 such that the sensitive volume is reduced when a detector element 21 collects radiation having traversed the body region in question during the CT scan.

Further, in case predefined control profiles are used as explained above, these control profiles may also take account of object regions with weak x-ray attenuation. So, control profiles for classes of objects including such a region may be generated on the basis of typical three-dimensional contours of such regions and on the basis of typical positions of such regions within the object in such a way that the sensitive volume of a detector element 21 is reduced when it collects radiation having traversed such a region in accordance with the considered contour and position of the region. When the contour and positions of relevant object regions are estimated in such a way, appropriate margins are preferably taken into account in view of deviations between the typical contours and positions of the regions in questions and the actual contours and positions of the regions in the objects to be imaged.

Although the aforementioned embodiments of the invention specifically relate to a use of the invention in a CT apparatus, the invention is not so limited. Rather, the invention can similarly also be applied in other x-ray devices comprising a radiation detector 1 having one or more detector elements 21, the sensitive volume of which can be adjusted separately from other detector elements 21. In case the radiation detector 3 and the x-ray source do not rotate around the object 41 to be imaged, control settings for adjusting the sensitive volume may be derived on the basis of x-ray images acquired with reduced radiation intensity before the actual x-ray image is acquired in a similar way as described above. As an alternative, the control settings may be derived on the basis of an estimated object contour determined using an object scanner or on the basis of a predefined contour for the class of the object to be imaged.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. An x-ray device for acquiring image data of an object to be imaged, the device comprising an x-ray source and a radiation detector,
    the radiation detector including detector elements for detecting radiation, each detector element comprising an adjustable sensitive volume, where an x-ray photon entering the sensitive volume produces an electric signal used for generating the image data,
wherein the device further comprises a control unit configured to control the sensitive volume of at least one of the detector elements in accordance with a geometric structure of the object to be imaged.

2. The x-ray device as defined in claim 1, wherein the control unit is configured to reduce the sensitive volume of the detector element when at least part of the detector element is located outside a shadow region created by the object in accordance with the geometric structure of the object.

3. The x-ray device as defined in claim 1, wherein the control unit is configured to reduce the sensitive volume of the detector element when at least part of the detector element collects radiation having traversed a region of the object having a smaller x-ray attenuation coefficient than another region of the object.

4. The x-ray device as defined in claim 1, the x-ray source and the radiation detector are configured to rotate around the object during an x-ray scan of the object.

5. The x-ray device as defined in claim 4, wherein a control profile indicates values of a control parameter for controlling the sensitive volume of the detector element for several positions of the radiation detector during the x-ray scan, and wherein the control unit controls the sensitive volume of the detector element by varying the control parameter in accordance with the values of the parameter indicated in the control profile.

6. The x-ray device as defined in claim 5, wherein the control unit is coupled to a storage for storing the control profile and wherein the control unit reads the control profile in connection with an execution of the x-ray scan.

7. The x-ray device as defined in claim 5, wherein the control unit is configured to generate the control profile on the basis of one or more images of the object acquired in a further x-ray scan, particularly in a scout scan.

8. The x-ray device as defined in claim 5, wherein the control unit is configured to generate the control profile in accordance with an estimated geometric structure of the object.

9. The x-ray device as defined in claim 8, further comprising a rangefinder device configured to scan the object, wherein the control unit is configured to estimate the geometric structure of the object on the basis of dimensions of the object determined using the rangefinder device.

10. The x-ray device as defined in claim 5, wherein predetermined control profiles for geometric structures for plural classes of the object are stored in the control unit and wherein the control unit is configured to select the control profile on the basis of an information about the class of the object to be imaged.

11. The x-ray device as defined in claim 1, wherein detector element comprises a converter element producing electric charge carriers in response to an incident photon, the converter element being arranged between a cathode electrode assembly and an anode electrode assembly, the anode electrode assembly comprising at least one anode electrode for collecting charge carriers to produces an electric signal used for generating the image data and at least one steering electrode which can be held on the same or a more negative electric potential than the anode electrode.

12. The x-ray device as defined in claim 11, wherein the sensitive volume of the detector element is reduced by bringing the electric potential of the steering electrode closer to the electric potential of the anode electrode or by making it more positive than the electric potential of the anode electrode.

13. The x-ray device as defined in claim 11, wherein a control profile indicates values of a parameter indicative of a voltage between the anode electrode and the steering electrode for several positions of the radiation detector during an x-ray scan, and wherein the control unit is configured to control the sensitive volume of the detector element by varying the voltage in accordance with the values of the parameter indicated in the control profile.

14. A method for operating an x-ray device to acquire image data of an object to be imaged, the device comprising an x-ray source and a radiation detector, the radiation detector including detector elements for detecting radiation, each detector element comprising an adjustable sensitive volume, where an x-ray photon entering the sensitive volume produces an electric signal used for generating the image data,
    wherein a control unit of the device controls the sensitive volume of at least one of the detector elements in accordance with a geometric structure of the object to be imaged.

15. A computer program executable in a processing unit of an x-ray device, the computer program comprising program code means for causing the processing unit to carry out a method as defined in claim 14 when the computer program is executed in the processing unit.

* * * * *